(12) United States Patent
Gittleman

(10) Patent No.: US 6,213,773 B1
(45) Date of Patent: Apr. 10, 2001

(54) REDUCED HEIGHT DENTAL IMPRESSION POST

(76) Inventor: Neal B. Gittleman, 14 Greenway Plaza #28E, Houston, TX (US) 77046

( * ) Notice: Subject to any disclaimer, the term of this patent is extended or adjusted under 35 U.S.C. 154(b) by 0 days.

(21) Appl. No.: 09/309,477

(22) Filed: May 10, 1999

(51) Int. Cl.[7] .................................................. A61C 13/225
(52) U.S. Cl. ............................................ 433/172; 433/214
(58) Field of Search .................................... 433/172, 173, 433/174, 213, 214

(56) References Cited

U.S. PATENT DOCUMENTS

| | | | | |
|---|---|---|---|---|
| 4,854,872 | * | 8/1989 | Detsch ................................. | 433/173 |
| 5,108,288 | * | 4/1992 | Perry ................................... | 433/173 |
| 5,195,891 | * | 3/1993 | Sulc .................................... | 433/173 |
| 5,538,426 | * | 7/1996 | Harding et al. ...................... | 433/172 |
| 5,688,123 | * | 11/1997 | Meiers et al. ....................... | 433/173 |
| 5,697,779 | * | 12/1997 | Sachdeva et al. ................... | 433/2 |
| 5,782,918 | * | 7/1998 | Klardie et al. ...................... | 623/16 |

* cited by examiner

Primary Examiner—John J. Wilson
Assistant Examiner—Melba Bumgarner
(74) Attorney, Agent, or Firm—Ezra L. Schacht

(57) ABSTRACT

An apparatus comprised of dental implant impression mounting hardware with a non-interfering, low profile for making time saving and accurate, simultaneous upper and lower impressions with the mouth completely closed and the jaw accurately positioned in a resting position. A low profile cross bar or t-bar impression post snaps and holds securely within a self-curing elastomeric impression material, yet does not interfere with the taking of a simultaneous upper and lower elastomer impression of the accurately interdigitated jaw using a 'triple tray'. The cross bar or t-bar mounts to a perimucosal extension of selectable height. The cross bar assembly and the extension accurately clock and lock to the mating endo-osseous implant fixture or to the implant analog for excellent registration.

9 Claims, 5 Drawing Sheets

REDUCED HEIGHT DENTAL IMPRESSION POST

BACKGROUND OF THE INVENTION

In the field of dental implants, patient comfort and the efficient use of a dentist's time are paramount. Likewise, precision alignment of the prosthetic components are essential. The need to match both natural and artificial upper and lower teeth to within 5 microns and provide accurate mating of the prosthesis with existing teeth requires accurate replication of oral structures when making dental impressions. To create these accurate models and the final prosthesis, a matched upper and lower impression can be obtained simultaneously with the jaw in the closed position and the teeth in the interdigitated position (centric occlusion). Currently, the impression transfer posts used to register the implants to the upper and lower jaws prevent the full closure of the mouth while making the simultaneous upper and lower impressions. The present invention remedies this oversight.

SUMMARY OF THE INVENTION

After dental implants have healed into the underlying bone structures of the mandible or maxilla and the soft gum tissue has healed, a full set of upper and lower impressions of the mouth are made using individual full or partial arch upper and lower trays. Positive casts of these impressions are mounted upon a mechanical articulator which mimics the motion of the temporo mandibular joint (tmj). These positive casts are equipped with accurately placed implant fixture analogs positioned to accurately replicate the structures in the mouth.

To make an accurate impression, the healing caps are removed from one or more dental implant fixtures and impression transfer posts are accurately placed with retaining screws on each implant fixture. X-rays are taken to verify the proper seating of the impression transfer post. An impression tray filled with an self-hardening elastomeric impression material is pressed over the region of the dental arch containing the impression transfer posts. After a few minutes, the elastomeric impression material has set and the impression is removed with a gentle parting pressure. The impression transfer post is removed from the dental implant and the healing cap replaced. An analog of the dental implant is accurately attached to the impression transfer post which is replaced in the elastomeric impression, taking care to positively seat the transfer post. A stone model of the mouth structure with the dental implant analog exactly aligned and retained is created from the impression. This model with dental implant analogs cast in the properly aligned position is used to build the final prosthesis.

The elastomeric impression materials, such as polyvinylsiloxane or polyether, are dimensionally stable, but need adequate surface area in contact with the impression transfer post to ensure accurate replication of the implant within the models mounted upon the articulator. Currently, long tapered impression transfer posts are used, which have adequate surface area to accurately register the elastomeric impression to the dental implant analog. The height of these anchor posts prevents the quick and accurate use of a time saving triple tray when making simultaneous, closed jaw, upper and lower impressions.

To make an accurate impression of the upper and lower teeth in the correct alignment, a triple tray may be used. This tray consists of a molded plastic assembly with a handle connected to a set of confining dams and a thin open screen mesh. The mesh is oriented horizontally and is to be placed between the mating occlusal surfaces of the teeth while the jaw is in the closed or centric position. The buccal and lingual dams are molded to the mesh. A paste of quick setting elastomer is placed on both sides of the mesh within the confines of the dams. The mouth is closed with the upper and lower teeth in the closed or centric position while imbedded within the curing elastomer. In this manner, a matching set of aligned upper and lower impressions are made.

Instead of taking three time consuming, separate impressions of the upper arch, lower arch and bite, a single impression is made, thus the 'triple tray' name. If a single area of the partially edentulous mouth is being modeled, a half-arch, triple tray can be used.

A BRIEF DESCRIPTION OF THE DRAWINGS

FIG. 1 details a perspective view of an anterior triple tray,

FIG. 2 shows a typical conic impression post,

FIG. 3 details a low profile cross bar post, and

A DETAILED DESCRIPTION OF THE DRAWINGS

Figure 1:
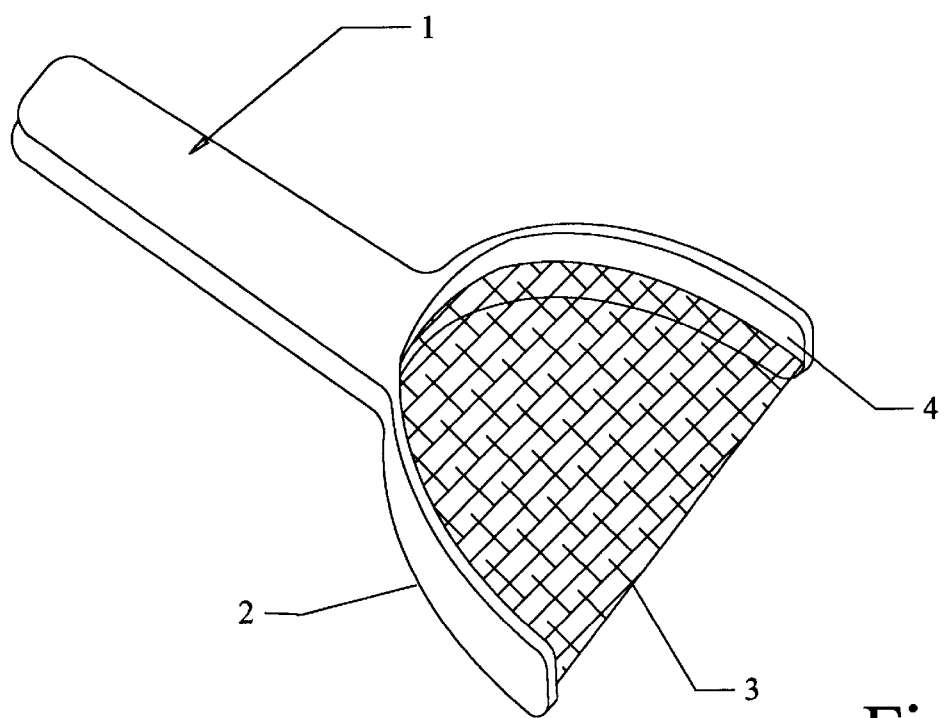

An accurate model can be fabricated from an impression of the upper and lower jaws with remaining natural teeth and dental implants by means of a triple tray. FIG. 1 shows a typical molded plastic anterior triple tray with handle 1, curved outer dam wall 2 and horizontal open mesh 3. A quick setting polymer paste is placed in an arc on both upper and lower sides of the mesh 3 against the inner dam wall 4. The dentist places the triple tray in the patient's mouth and closes the jaw in a natural occluded centric position. The thin loose mesh conforms to the touching occlusal surfaces of the upper and lower teeth while the polymer completely enfolds the teeth, implants and other structures to form an accurate impression. A plastic, lingual side dam molded to the mesh can be present but is now shown in this drawing.

Figure 2:
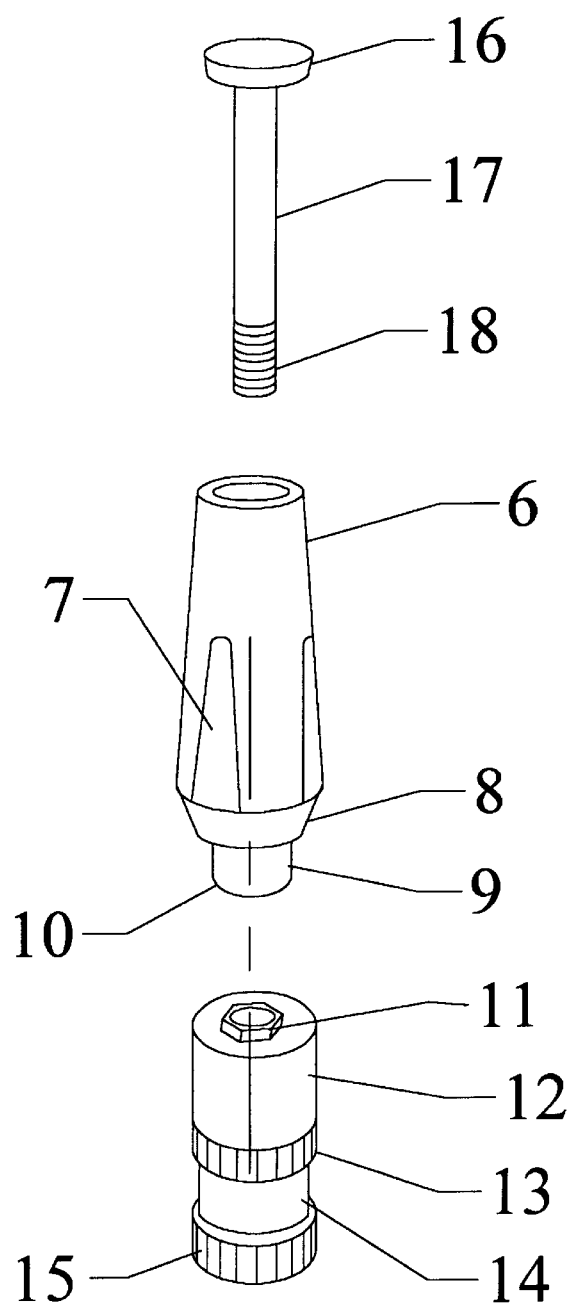

A typical impression post, detailed in FIG. 2, consists of a metal cylindrical or conic body 6 having flats 7 to prevent rotation when imbedded in the elastomeric impression. Soft tissue emergence taper 8 and collar 9 mimic the profile of the permanently installed abutment used to secure the final prostheses. An internal hex pattern 10 is used to clock or radially align the impression post upon the external hex 11 of a dental implant (not shown) and the implant analog post 12 (shown). This assures proper clocking or radial alignment. Knurled regions 13 and 15 and undercut region 14 securely lock the implant analog post in the plaster replica of the mouth region being modeled. Retaining screw 17 has a wide head 16 acting to positively lock the impression transfer post 6 within the elastomeric mold by means of a positive snap or detent. This snap is distinctly felt as the impression transfer post is reseated firmly in the elastomeric mold. Screw threads 18 mate with internal threads within the implant fixture analog 12.

Figure 3:
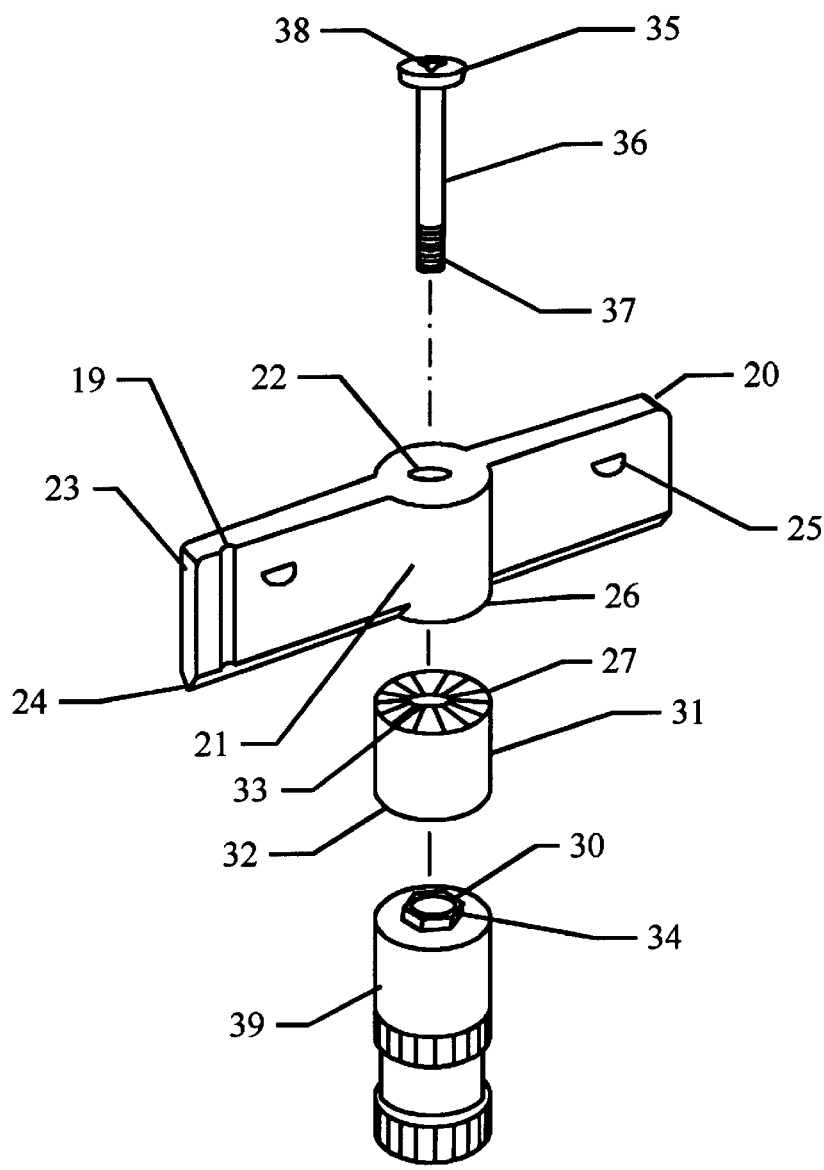

The inventor, in order to prevent the interference of installed upper and lower impression posts while taking simultaneous upper and lower impressions with a triple tray, details a new type of low profile, cross bar impression post 21 in FIG. 3. This horizontal cross bar impression post 21 mounts to a perimucosal extension element 31. The cross section profile 23 of the cross bar 20 has sharp lower edge 24 to cut through and part any solidified elastomeric compound to aid in extracting the impression. The cross bar has detent means 25 to provide a positive snap or detent and to prevent the cross bar from withdrawing from the cured impression compound. The cross bar 20 offers the same or more surface area and embedded structure as a conventional impression post for dimensional stability while having a lower profile to prevent interference with structures on the opposing dental arch with the mouth closed in the centric position. The perimucosal extension element 31 is fabricated in a number of fixed heights to accommodate various tissue and mounting height conditions in the mouth. This extension element 31 has a serrated radial pattern 27 to clock and lock the extension element to the matching pattern 26 on underside of the cross bar impression post 21. Similarly, a radially symmetrical pattern such as a hex or octagonal depression 32 on the underside of extension 31 clock and lock with the hexagonal or octagonal radial pattern 34 of the implant analog 39 for near perfect alignment. The inventor has found that the ability to rotate or clock the extension element by 15 degrees is sufficient to anticipate all installation circumstances. This would require twenty-four radial serrations between surfaces 26 and 27. Any other matching pattern with radial symmetry that will clock and lock the extension 31 to the low profile cross bar impression transfer post 21 can be used. Methods of manufacturing the serrations include casting, milling or machining, embossing with a hardened die, photo masking and chemical etching, wire or die sinking Electrical Discharge Machining (EDM), or other economical methods. A mounting means such as a retaining screw 36 passes through hole 22 in the cross bar impression post 21, passes through the perimucosal extension element 31 with through hole 33 and into internally threaded mounting hole 30 in the implant analog post 39. External screw threads 37 mate with internal threads within implant analog post 39.

In one embodiment of the invention, special drive means 38 have at least three lobes with near vertical walls to improve retaining screw locking torque. An friction drive screw head without indented pattern also can be used.

A polarizing groove 19 prevents the cross bar impression post from being installed in the wrong direction. A flat (not shown) on the barrel portion of cross bar impression post could be used for polarization.

Externally visible matching registration marks to aid in the proper radial alignment of the cross bar impression transfer post 21 and extension element 31 can be included.

Though, the extension element 31 is shown as a cylinder, it can have a contoured emergence profile to better match the natural gingival margins of a natural tooth, both for better aesthetics and hygiene.

The extension element 31 can have a lower clocking and locking surface that mates with the coronal locking means of existing implants presently available from the leading manufacturers of implants. These would include hexagonal or octagonal patterns or other radial alignment techniques.

Figure 4:
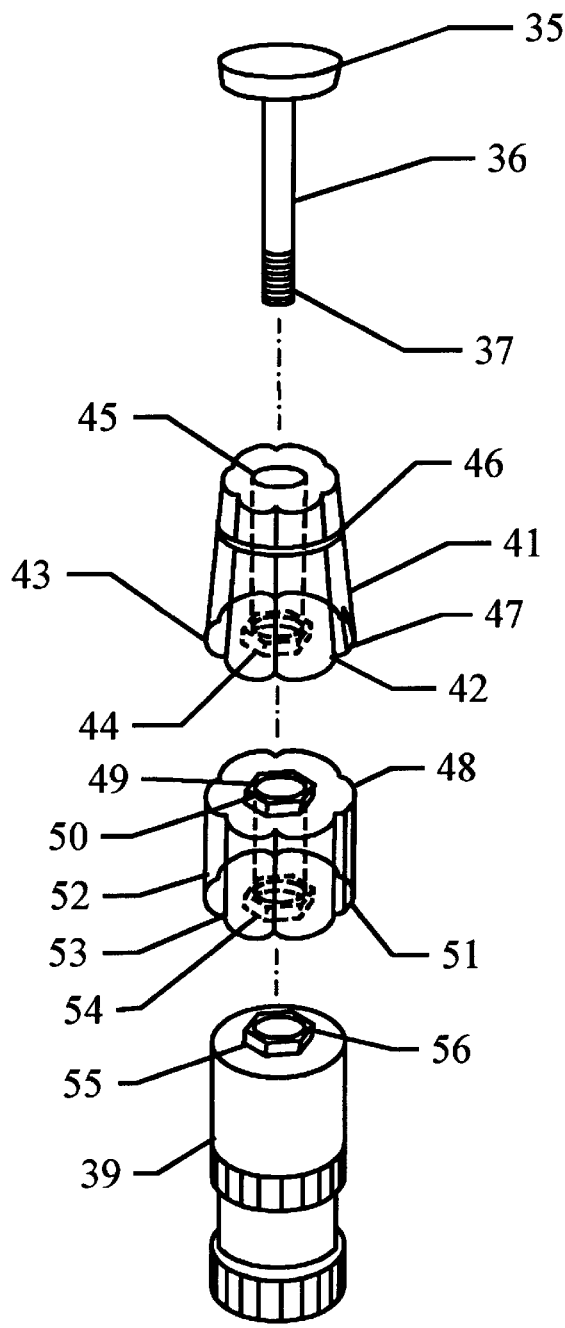
FIG. 4 is a perspective view of a corrugated surface low profile impression transfer post with associated hardware.

The extension element 31 can have an upper clocking and locking surface that mirrors its lower clocking and locking surface. In this way, the extension element simply acts to extend the coronal aspect of the implant fixture in perfect radial alignment and coplanarity the proper distance above the soft tissue line. In FIG. 4, as an example, a positively projecting hexagonal locking and clocking pattern 55 on the coronal aspect of an implant analog from a leading manufacture fits into a matching hexagonal recess on the lower surface 54 of extension element 48. The upper surface of the extension element has a positive matching hexagonal clocking and locking pattern 50 in radial and coplanar alignment with the hexagonal recess 54 on the lower surface. Thus the clocking and locking pattern is transferred accurately from the top of the analog 39 to the top of the perimucosal extension 48. The implant analog has the same coronal clocking and locking pattern as the implant itself.

The retaining means can consist of a retaining screw 36 with an extended, taller head 35 to be used in cases requiring open topped impression trays.

In the embodiment of the invention, as detailed in FIG. 4, a low profile impression post 41 is fabricated as a tapered conic section with corrugated crests 43 and corrugated valleys 42 to increase the surface area for retention within the elastomeric impression compound. By increasing the surface area and by having an adequate number of crests, the conic section will be prevented from rocking or rotating within the cured firm elastomer. This will guarantee accurate registration while offering a non interfering low profile impression post in keeping with the objectives of the invention. A circumferential groove 46 or other detent means gives a positive snap when the impression post is replaced into the elastomeric impression material. A polarizing flat 47 or other polarizing means insures that the impression post is properly oriented upon replacement in the elastomeric impression material. A matching flat 51 is shown extended along the side of perimucosal extension 48. Drive screw 36 with friction drive head 35 passes through hole 45 and hole 49. Threads 37 on drive screw 36 engage into internal threads hole 45 in analog fixture 39.

A matching optional perimucosal extension post 48 can be used to adjust the height of the impression transfer post 41, having corrugated crests 52 and valleys 53, at least above the soft tissue line.

Figure 5:
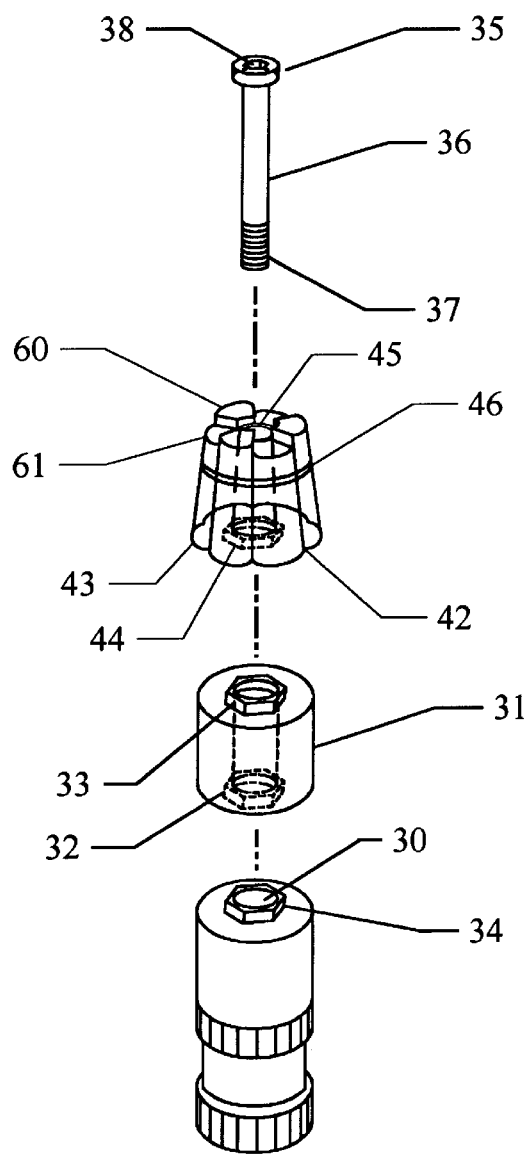
FIG. 5 is a perspective view of a crenelated upper surface low profile impression transfer post with associated hardware.

In another embodiment of the invention, as shown in FIG. 5, a crenelated or crowned, top surface 60 and 61, conic low profile impression post 31 will clock and lock within the elastomer, in keeping with the objectives of the invention. The crenellations can be extended as ribs 43 and grooves 42 down along the sides of the impression post. The increased surface area of these anti-rotation ribs increase the stability and accuracy of this low profile impression transfer post. Retaining means similar to drive screw 36 in FIG. 4 can be used to secure the crenelated impression transfer post.

What is claimed is:

1. In an apparatus for accurately aligning an analog of a dental implant fixture within a cast model of mouth structures containing at least one healed dental implant modeled from a single, simultaneous impression of the upper mouth, lower mouth and bite registration with the jaw in the closed position and the teeth in the interdigitated position wherein the improvement comprises: at least one low profile, non-interfering, cross bar impression transfer post having two generally rectangularly shaped wings extending laterally for embedding in elastomeric impression compound;

in combination with at least one perimucosal extension with clock and lock pattern on top and bottom surfaces; and a mounting means for retaining said at least one low profile cross bar impression transfer post through said at least one perimucosal extension to the dental implant fixture.

2. In an apparatus as described in claim 1, comprising:
   said at least one low profile, non-interfering, cross bar impression transfer post having detents located upon said two generally rectangularly shaped wings extending laterally to positively snap within said elastomeric compound.

3. In an apparatus as described in claim 1, comprising:
said at least one low profile, non-interfering, cross bar impression transfer post having polarizing means located upon said two generally rectangularly shaped wings extending laterally to insure proper insertion.

4. In an apparatus for accurately aligning an analog of a dental implant fixture within a cast model of mouth structures containing at least one healed dental implant modeled from a single, simultaneous impression of the upper mouth, lower mouth and bite registration with the jaw in the closed position and the teeth in the interdigitated position wherein the improvement comprises:

at least one non-interfering, low profile corrugated conical impression transfer post having vertical ribs and grooves on the external conic surface for embedding in elastomeric impression compound;

in combination with at least one corrugated perimucosal extension having vertical ribs and grooves on the external surface of said perimucosal extension configured to match the external surface of said impression transfer post, with clock and lock pattern on top and bottom surfaces; and a mounting means for retaining said at least one non-interfering, low profile corrugated conical impression transfer post through said at least one perimucosal extension to dental implant fixture.

5. In an apparatus as described in claim 4, comprising:
said at least one non-interfering, low profile corrugated conical impression transfer post having detents located upon the external conic surface to positively snap within said elastomeric compound.

6. In an apparatus as described in claim 4, comprising:
said at least one non-interfering, low profile corrugated conical impression transfer post having polarizing means located upon the external conic surface to ensure proper insertion.

7. In an apparatus for accurately aligning an analog of a dental implant fixture within a cast model of mouth structures containing at least one healed dental implant, wherein the improvement comprises:

at least one non-interfering, low profile conical impression transfer post having a crenelated upper surface with multiple stepped flats and having side ribbed and grooved corrugations vertically extending externally along the conic surface for engaging in elastomeric impression compound;

in combination with at least one perimucosal extension with clock and lock pattern on to and bottom surfaces; and a mounting means for retaining said at least one low profile crenelated upper surface and side ribbed and grooved impression transfer post through said at least one perimucosal extension to the dental implant fixture.

8. In an apparatus as described in claim 7, said at least one impression transfer post having a crenelated upper surface with multiple stepped flats and side ribbed and grooved corrugations vertically extending externally along said conic surface comprising: detents located upon the external conic surface to positively snap within said elastomeric compound.

9. In an apparatus as described in claim 7, said at least one impression transfer post having a crenelated upper surface with multiple stepped flats and side ribbed and grooved corrugations vertically extending externally along said conic surface comprising: polarizing means located upon said external conic surface to ensure proper insertion.

\* \* \* \* \*